US00PP10837P

United States Patent [19]

van Andel

[11] Patent Number: Plant 10,837

[45] Date of Patent: Mar. 23, 1999

[54] ALSTROEMERIA PLANT NAMED 'STASABI'

[75] Inventor: Jacob van Andel, Aalsmeer, Netherlands

[73] Assignee: Van Staaveren b.v., Aalsmeer, Netherlands

[21] Appl. No.: 879,532

[22] Filed: Jun. 19, 1997

[51] Int. Cl.[6] ..... A01H 5/00

[52] U.S. Cl. ..... Plt./87.1

[58] Field of Search ..... Plt./87.1

[56] References Cited

PUBLICATIONS

Huxley et al. (Eds.) "Alstroemeria", The New R.H.S. Dictionary of Gardening, The Stockton Press New York. vol. 1 pp. 141–148, 1992.

*Primary Examiner*—Howard J. Locker
*Assistant Examiner*—Melissa L. Kimball
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 82R0473-6 and as pollen parent an unreleased, unpatented seedling identified as 86F1115-3 from among my collection of Alstroemeria seedlings maintained under controlled conditions in a greenhouse at Van Staaveren B.V., Aalsmeer, The Netherlands, for developmental purposes. The varietal denomination of the new variety is 'Stasabi'.

The first act of asexual reproduction of 'Stasabi' was in Aalsmeer, The Netherlands, by propagation by dividing rhizomes Asexual reproduction by dividing rhizomes in Aalsmeer, The Netherlands, has demostrated that the combination of characteristics as herein disclosed for 'Stasabi' are firmly fixed and retained through successive generations of asexual reproduction.

'Stasabi' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stasabi' are characterized by unusual coloration, as described herein.

DESCRIPTION OF ILLUSTRATION

The new variety of Alstroemeria hybrid as illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family.*—Liliaceae.
- *Genus.*—Alstroemeria sp.
- *Commercial.*—Alstroemeria hybrid.

Orgin: Seedling.

Plant

Form: Bush.
Shape: Upright.
Height: About 150 to 200 cm.
Internode length: About 1 to 10 cm.
Growth rate: Medium; the length of time (number of days) taken from young plants (rooted rootstocks, the stage of development in which the varieties are sold) to flowering stage under commercial greenhouse conditions is 80–90 days.
Main stem or cane length: About 175 cm; pinching not required.
Growth: Vigorous.
Strength: Strong.
Foliage:
- *Quantity.*—Abundant.
- *Number of leaves.*—About 35 to 45 per stem.
- *Size of leaf.*—Length: About 15 to 20 cm. Width: About 3 to 5 cm.
- *Shape of leaf.*—Elliptical.
- *Margin type.*—Entire.
- *Texture.*—Glossy.
- *Color.*—Upper side: Near 137A. Underside: Near 137C.
- *Rhizomes.*—Yes. Color: Near 155D. Size: About 10 to 30 cm.

Inflorescence—Flower/Floret

Blooming habit: Continuous; Spent umbels not required to be pinched to maintain the plant in a continuous blooming condition.
Blooms: Profusely.
- *Spring.*—Yes.
- *Fall.*—Yes.

Size:
- *Diameter.*—About 6 cm.
- *Depth.*—About 5 cm.

Borne: Singly.
Shape or form:
- *When bloom first opens.*—Cup.
- *When bloom matures.*—Cup.
- *Number of tepals.*—6.
- *Arrangement.*—2 concentric circles of 3 tepals.
- *Form.*—Obovate.
- *Apex.*—Pointed.
- *Duration of tepals on stem?*—About 3 weeks.
- *Texture.*—Soft.

*Appearance.*—Velvety.

*Color* (*summer/fall*).—Outer tepal/floret: Body near 27A/45C; base near 27A; reverse side near 27A/45C. Inside tepal/floret: Body near 3A/3C/45C; base near 3A; reverse side near 3A/3C/45C. Spots: The two inner lateral tepals have about 20–40 spots, color near 185A. The inner median tepal has no yellow part near 3A but only a yellow part near 3C and about 10–20 small spots, color near 185A.

Peduncle or flower stem:

*Length.*—About 10 to 15 cm.

*Color.*—Near 137B.

*Strength.*—Strong.

*Upright.*—Yes, not hairy.

No discoloration after full bloom and not affected by wet or hot weather.

Persistence: No.

Disease resistance: Unknown.

Fragrance: None.

Lasting quality:

*On plant.*—About 3 weeks.

*As cut flower.*—About 14–16 days.

Bud

Size:

*Diameter.*—About 1 to 2 cm.

*Depth or length.*—About 2 to 4 cm.

Form or shape: Pear-shaped, long.

Rate of opening: Fast.

Color of tepals/florets:

*When tepals begin to unfurl.*—Near 3A/3C/45C.

*When tepals first divide.*—Near 3A/3C/45C.

Reproductive Organs

Stamen:

*Number.*—6.

*Arrangement.*—Around the style, side-by-side.

Anthers:

*Size.*—About 8 to 10 mm.

*Color.*—Near 164B.

Filaments:

*Length.*—About 5 cm.

*Color.*—Near 39C.

Pollen:

*Color.*—Near 165A.

Pistils:

*Number.*—1.

Styles:

*Length.*—About 4 to 5 cm.

*Color.*—Near 37A.

Stigmas:

*Color.*—Near 37A.

Fruit

Fertile: Yes.

Shape: Round.

Color at maturity: Near 163A.

I claim:

1. A new variety of Alstroemeria plant substantially as herein described and shown.

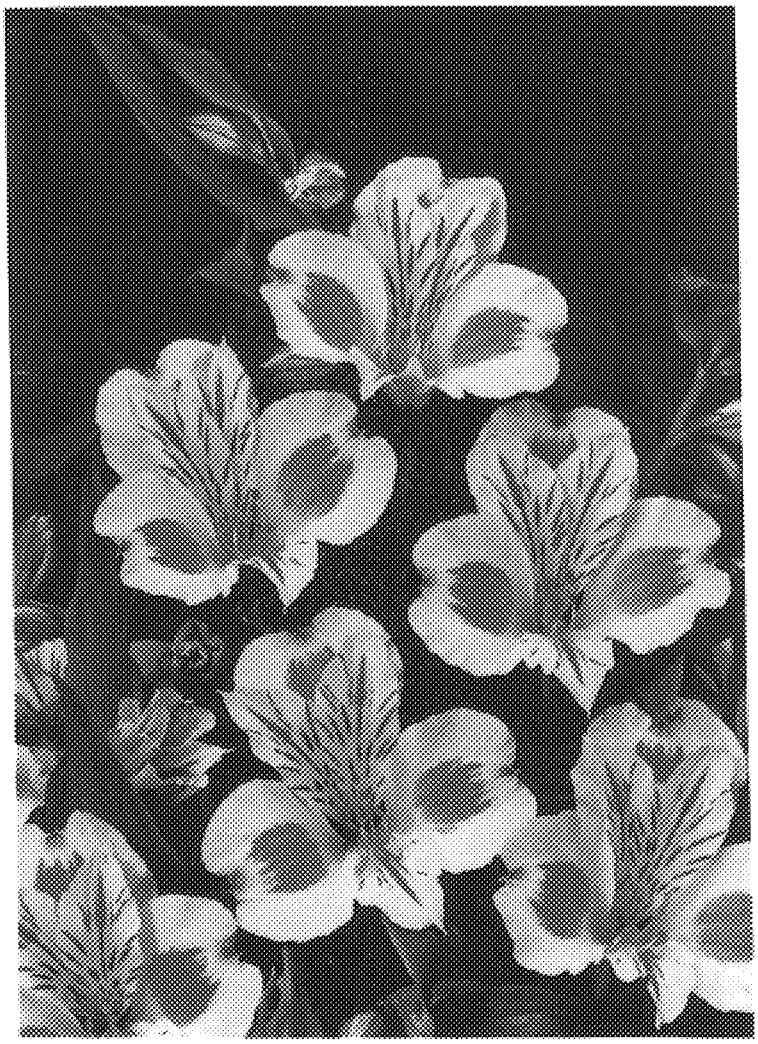

* * * * *